United States Patent [19]

Rothman et al.

[11] 4,126,669
[45] Nov. 21, 1978

[54] DIAGNOSTIC AGENT

[75] Inventors: Ulf S. E. Rothman, Höllviksnäs; Bernt J. Lindberg, Upsala, both of Sweden

[73] Assignee: Pharmacia Aktiebolag, Upsala, Sweden

[21] Appl. No.: 767,197

[22] Filed: Feb. 9, 1977

Related U.S. Application Data

[63] Continuation of Ser. No. 583,212, Jun. 2, 1975, abandoned.

[51] Int. Cl.² ............... A61K 29/00; A61K 43/00
[52] U.S. Cl. ............................. 424/1; 128/2 A; 252/301.1 R; 424/1.5; 424/9
[58] Field of Search ............... 424/1, 12, 180, 9, 1.5; 128/2 A; 252/301.1 R

[56] References Cited

U.S. PATENT DOCUMENTS

| 3,663,685 | 5/1972 | Evans | 424/1 |
| 3,758,678 | 9/1973 | Lindsay et al. | 424/1 |

OTHER PUBLICATIONS

Lowe and Dean, Affinity Chromatography, Wiley and Sons, N.Y., 1974, pp. 201, 249.

Primary Examiner—Benjamin R. Padgett
Assistant Examiner—Christine M. Nucker
Attorney, Agent, or Firm—Fred Philpitt

[57] ABSTRACT

A diagnostic agent for intravascular administration into blood vessels composed of radioactively labelled particles suspended in a physiologically acceptable aqueous liquid, said particles having a size so selected that they clog fine blood vessels having a diameter within the range 5 - 300 μm, said particles consisting of a three-dimensional, water-insoluble, hydrophilic, swellable, cross-linked network of polysaccharide substances, and the method of using this diagnostic agent.

14 Claims, No Drawings

DIAGNOSTIC AGENT

This is a continuation of application Ser. No. 583,212, filed June 2, 1975, abandoned. The present invention relates to a diagnostic agent for intravascular administration, said agent consisting of or containing a suspension of minute particles and a radioactive substance.

It is previously known to use suspensions of minute, preferably spherical particles of different materials labelled with radioactive isotopes for intravascular administration to animals and humans for diagnostic purposes. Particles preferably used for this purpose are prepared from protein such as serum albumin. Such radioactive serum albumin particles are described for example in the German Published Specification No. 1,916,704, Particles based on polysaccharides or on synthetic polymers (e.g. polystyrene) and even on inorganic materials labelled with radioisotopes have also been used experimentally for intravascular administration in tests carried out on animals.

The particles previously tested in this regard are encumbered with a number of disadvantages. One such disadvantage resides in the fact that some particles do not decompose or decompose too slowly in the blood vessels and remain more or less permanently in said vessels. They can give rise to small thromboses which do not regress, even should the particles be subsequently dissolved or decomposed and leave the blood vessel in question, which obviously leads to serious consequences. Another disadvantage resides in the fact that most of the previously tested particles, for example albumin-based particles, exhibit poor suspension stability and are prone to sedimentation and/or conglomeration (e.g. owing to the high specific weight and/or the adhesiveness of the particles) rendering it necessary to subject the suspension to ultrasonic treatment in order to prevent this from happening. However, the stability of such eariler particle suspensions treated ultrasonically is very poor and the suspension must be used as soon as possible after said treatment. The stability of the particles (for example the albumin particles) is often so poor as to render it necessary to store said particles in freeze dried condition, the durability of the particles being, nevertheless, still limited. Some particles are unable to withstand variations in temperature and cannot be sterilized by heat treatment. The previously tested particles have either not been dissolvable or degradable in blood plasma, or have been dissolvable or degradable only in an irregular and non-reproducable manner, or have been changed in this regard during storage, which presents considerable disadvantages and risks.

It has been surprisingly discovered that the aforementioned disadvantages encountered with the previously used particles can be eliminated by means of the present invention.

The present invention relates to a diagnostic agent which is intended to be administered intravascularly and which consists of or contains a suspension of minute particles, preferably having a particle size in the order of magnitude of 0.1 – 300 $\mu$m (micrometer), comprising a polysaccharide built up of glucose units, or a physiologically acceptable derivative of said polysaccharide in a physiologically acceptable aqueous liquid, said suspension also comprising a radioactive substance which is bound to and/or enclosed in and/or in mixture with said minute particles.

The diagnostic agent according to the invention is characterized in that the aforementioned particles comprise a water-insoluble but hydrophilic, swellable (i.e. swellable in water), three-dimensional network of molecules of the polysaccharide or the derivative thereof cross-linked by bridges having bonds of a covalent nature, said network being degradable by $\alpha$-amylase in blood plasma into water-soluble fragments, either directly or subsequent to a preceding splitting-off of possibly occurring substituents, preferably glucoside bound and/or ester bound substituents, in the polysaccharide by the action of an enzyme, preferably glucosidase and/or esterase, in blood plasma.

The polysaccharide which is built up of glucose units and which shall be incorporated (as such or in the form of a physiologically acceptable derivative) in cross-linked form in the particles, shall be capable of beig degraded by $\alpha$-amylase into water-soluble fragments, i.e. the polysaccharide shall contain $\alpha$ (1 → 4) glucosidic linkages which are hydrolyzable by $\alpha$-amylases. Examples of such polysaccharides include primarly starch and glycogen or dextrins thereof. The starch may be amylose or amylopectin or mixtures thereof. Other glucose-containing polysaccharides which can be hydrolyzed by $\alpha$-amylase can also be used, in connection with which said polysaccharides may be synthetic or may be obtained from biological material, for example from microogranisms. It is simplest and cheapest, however, to use starch in the form of amylose or amlopectin or mixtures thereof. Similarly, the physiologically acceptable derivative of the polysaccharide shall be degradable by $\alpha$-amylase directly or subsequent to a preceding splitting-off of substituents under the action of an enzyme in blood plasma, such as for example esterases or glucosidases. Substituents in the polysaccharide may, for example, be hydroxyalkyl groups (which are optionally broken by one or more oxygen atoms), for example lower hydroxyalkyl groups having for example 2 – 6 carbon atoms such as 2-hydroxyethyl, 2-hydroxypropyl and/or 2,3-dihydroxypropyl, and/or alkyl groups, e.g. lower alkyl groups having 1 – 6 carbon atoms such as methyl and/or ethyl, and/or substituted alkyl groups, e.g. substituted with carboxyl groups such as carboxy methyl and/or alkanoyl groups, or substituted alkanoyl groups, e.g. lower alkanoyl groups having e.g. 2 – 6 carbon atoms, such as acetyl, propionyl, 2-hydroxypropanoyl, succinoyl and/or glutaroyl. The reducing end group of the polysaccharide may be unchanged or modified. For example, it may be oxidized or reduced, so that said end of the polysaccharide chain is terminated with a carboxyl group or a primary hydroxyl group. It may, for example, also be present in the form of a glucoside, e.g. with an alcohol such as glycerol.

The cross-linking bridges may be bound to the molecules of the polysaccharide or the derivative thereof over different types of bonds. In accordance with a particularly suitable embodiment of the invention, these bonds are ether bonds. In accordance with a further suitable embodiment of the invention, said bonds are ester bonds, the term ester bonds being used here in its widest significance. Thus, the term also includes for example, carbomic acid ester bonds and thiocarbamic acid ester bonds. Preferably, aliphatic bridge building links are chosen, although said links may also be, for example, aromatic or araliphatic.

The cross-linking bridges may also contain to advantage hydrophilic groups, e.g. hydroxyl groups (e.g. one to six hydroxyl groups in each bridge).

In accordance with the invention, the cross-linked polysaccharide molecules in the practically infinite three-dimensional network may be substituted with other substituents than the cross-linking bridges. For examples, these substituents may be one or more of the aforementioned substituents, e.g. hydroxyalkyl, alkyl and/or alkanoyl. As will be readily understood, monofunctionally bound substituents originating from the cross-linking agent may also occur.

In accordance with a particularly suitable and practical embodiment of the invention, the molecules of the polysaccharide or of the derivative thereof are cross-linked by means of bridges which are bound to these molecules over ether bonds, wherein the bridges between the ether bonds may advantageously be straight or branched aliphatic saturated hydrocabon chains which are substituted by one or more hydroxyl groups (e.g. one to six hydroxyl groups) and which contain 3 – 30 carbon atoms, preferably 3 – 20 carbon atoms, such as 3 – 10 carbon atoms, and which are optionally broken by one or more oxygen atoms (e.g one to six oxygen atoms). Examples of such ether-bound cross-linking bridges are —$CH_2$ . $CH(OH)$ . $CH_2$— and —$CH_2$ . $CH(OH)$ . $CH(OH)$ . $CH_2$— and

—$CH_2$ . $CH(OH)$ . $CH_2$ . O . $CH_2$ . $CH(OH)$—$CH_2$— and

—$CH_2$ . $CH(OH)$ . $CH_2$ . O . $(CH_2)_n$ . O . $CH_2$ . $CH(OH)$ . $CH_2$—, where n is an integer, for example an integer from 2 to 4, and $$—CH_2 . CH(OH) . CH_2 . O . \overset{\overset{CH_3}{|}}{CH} . CH_2 . CH_2 . O . CH_2 . CH(OH) . CH_2—$$

and

—$CH_2$ . $CH(OH)$ . $CH_2$ . O . $CH_2$ . $CH_2$ . O . $CH_2$ . $CH_2$ . O . $CH_2$ . $CH(OH)$ . $CH_2$— and

—$CH_2$ . $CH(OH)$ . $CH_2$ . O . $CH_2$ . $CH(OH)$ . $CH_2$ . O . $(CH_2)_n$ . O . $CH_2$ . $CH(OH)$ . $CH_2$ . O . $CH_2$ . $CH(OH)$ . $CH_2$—, where $n$ is an integer, for example an integer from 2 to 4.

In accordance with another embodiment of the invention, the molecules of the polysaccharide or of the derivative thereof are cross-linked by means of bridges which are bound to said molecules over ester bonds which may preferably be carboxylic acid ester bonds, but which may also be carbamic acid ester bonds or thiocarbamic acid ester bonds, the bridges between the ester bonds advantageously being straight or branched aliphatic saturated hydrocarbon chains containing 2 – 20 carbon atoms, preferably 2 – 10 carbon atoms such as 2 – 6 carbon atoms, and being optionally broken by one or more oxygen atoms (e.g. one to six oxygen atoms) and optionally substituted with one or more hydroxyl groups (e.g. one to six hydroxyl groups).

Examples of such ester-bound (in its widest significance) cross-linked bridges are —O . CO . $(CH_2)_{n_1}$ . CO . O—, where $n_1$ is an integer, for example an integer from 1 to 20, preferably 2 – 10 such as 2 – , and —O . CO . $CH_2$ . O . $CH_2$ . CO . O— and —O . CO . NH . $(CH_2)_{n_2}$ . . NH . carbon . O— and —O . CS . NH . $(CH_2)_{n_2}$ . NH . CS . O—, where $n_2$ is an integer, for example an integer from 2 to 6.

In accordance with the invention, the three-dimensional network in question is capable of being degraded by α-amylase in blood plasma into water-soluble fragments, either directly or subsequent to a preceding splitting-off of possibly existing substituents in the polysaccharide under the action of an enzyme in blood plasma, for example, esterases or glucosidases. The degradation of the network by α-amylase takes place owing to the fact that α-amylase hydrolyses glucosidic linkages in the polysaccharide chains of the network. In order that the network should exhibit suitable properties with regard to the degradation of said network by α-amylase, it is generally suitable that the substitution degree of the polysaccharide with respect to the cross-linking bridge substituents and possible occurring singly bound substituents, which cannot be split-off by enzymes in blood plasma, is lower than 70 per cent, preferably lower than 60 per cent, said substitution degree being given as the percentage of the number of substituted glucose units with respect to the total number of glucose units present. For example, said substitution degree may be lower than 55 per cent, e.g. lower than 50 per cent. It is generally suitable for the substitution degree of the polysaccharide with respect to the cross-linking bridge substituents and possibly occurring singly bound substituents, which are not capable of being splitoff by enzymes in blood plasma, to be higher than 1 per cent, preferably higher than 2 per cent, said substitution degree being given as the percentage of the number of substituted glucose units with regard to the total number of glucose units present. For example, the substitution degree may be higher than 5 per cent, for example higher than 10 per cent. Generally, the substitution degree with respect to all kinds of substituents (I.e. the total substitution degree) is suitably lower than 80 per cent preferably lower than 70 per cent, for example lower than 60 per cent and suitably higher than 1 per cent, preferably higher than 2 per cent, for example higher than 5 per cent. Thus, for example, the substitution degree may be 35 per cent, i.e. of 100 glucose units in the polysaccharide chains 35 of these glucose units are carrying at least one substituent.

In accordance with the invention, the cross-linked polysaccharide product is insoluble in water but swellable in water to a gel. It may, for example, contain more than 50 per cent by weight of water, such as more than 60 per cent by weight of water, preferably more than 65 per cent by weight of water, for example more than 70 per cent by weight of water. It may, for example contain less than 99.8 per cent by weight of water, preferably less than 99.5 per cent by weight of water, such as less than 99 per cent by weight of water, generally less than 98 per cent by weight of water, such as less than 95 per cent by weight of water.

In accordance with the invention, the mesh size of the three-dimensional network may be such that protein molecules of the same order of magnitude as α-amylase are able to penetrate into the particles in their water-swollen condition. The mesh size can be determined with the aid of conventional gel chromatographic tests, using substances, such as proteins, of different molecular sizes.

In accordance with the invention, the three-dimensional network of the particles may be such that said network is broken up more slowly by α-amylase in the outer layer of the particle than in the inner part thereof. In this case, the three-dimensional network of the particle may exhibit a higher substitution degree of cross-linking substituents and/or monofunctionally bound substituents in the outer layer of the particle than in the inner part thereof.

The particles may have an irregular shape or may be spherical. Preferably, spherical particles are chosen. Preferably, the particles have substantially a particle size of the order of 0.1 - 300 μm (micrometer), e.g. 1 - 100 μm in water-swollen state. When it is desired to clog fine blood vessels, particles having a size of 5 - 60 μm in water-swollen state are often chosen.

In accordance with the invention, the particle size can be selected so that said particles clog fine blood vessels located in or leading to a selected portion of the body, subsequent to being administered intravascularly.

In this instance, the particle size is selected in dependence upon the dimensions of the blood vessels to be clogged. instances, for example An example of fine blood vessels of interest in this context is blood capillaries having a diameter of about 5 - 15 μm and metaarterioles having a diameter of about 15 - 300 μm. In certain instances,forexample when determining the volume of blood using radioactive particles, the selected size of the particles may be such that the particles do not fasten, even in the finest of blood capillares.

One advantageous embodiment of the invention is characterized in that the three-dimensional network can be degraded by α-amylase into water-soluble fragments having substantially a molecular weight beneath 50,000. In this way, the major portion of the fragments are excreted over the kidneys with the urine.

In accordance with the invention, the meshes of the three-dimensional network may be enlarged subsequent to cross-linking by partially degrading said network, e.g. by partial hydrolysis of glucosidic linkages in the cross-linked polysaccharide chains. Such a partial hydrolysis may be effected, for example, with an acid or α-amylase.

In accordance with the invention, subsequent to being injected into the blood vessels, the particles can be degraded into water-soluble fragments by α-amylase within, for example, the space of some few seconds to many hours, depending upon the effect desired in each individual case. With regard to the particles according to the invention, the degradation time may thus be varied within wide limits and can be well and reproductably established for the desired field of use.

The cross-linking of the polysaccharide molecules to a practically infinite three-dimensional network can be effected by reacting the polysaccharide or the polysaccharide derivative in question with an at least bifunctional cross-linking agent. Preferably, the cross-linking agent is reacted with hydroxyl groups in the polysaccharide chains whereby many bridges of the following type are obtained between the polysaccharide chains: $P_1 - O - B - D - P_2$, wherein $- B -$ is a bridge-forming link between oxygen atoms derived from hydroxyl groups in two different polysaccharide chains $P_1$ and $P_2$. Preferably, the bridge-forming link B contains at least 3 carbon atoms, for example 3 - 30 carbon atoms or 3 - 20 carbon atoms.

For the purpose of obtaining cross-linking bridges which are bound to the polysaccharide chains over ether bonds, the polysaccharide or the polysaccharide derivative can be reacted for example, in an alkaline aqueous solution with a cross-linking agent, for example of the type:

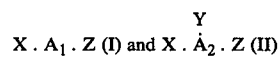

where X, Y and Z each represent a halogen atom, preferably chloro or bromo and $A_1$ and $A_2$ each represent a straight or branched aliphatic, saturated hydrocarbon chain which is substituted by one or more hydroxyl groups (e.g. one to six) and which preferably contains 3 - 30 carbon atoms, for example 3 - 20 carbon atoms, such as 3 - 10 carbon atoms and which is optionally broken by one or more oxygen atoms (e.g. one to six), or with a corresponding epoxide compound which can be obtained form the the compound (I) or (II) by splitting off hydrogen halide. Examples of bifunctional substances of the formula $X . A_1 . Z$ and corresponding epoxide compounds which can be obtained from coumpounds of said formula by splitting off hydrogen halide are:

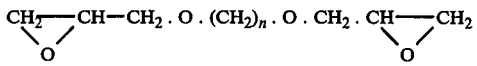

where n is an integer, for example from 2 to 4 and

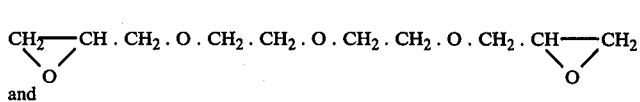

and

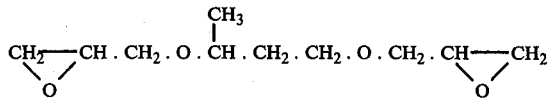

and

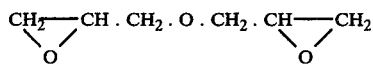

and

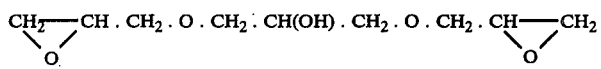

or corresponding halogen hydrins, and bifunctional glycerol derivatives of the formula $X \cdot CH_2 \cdot CH(OH) \cdot CH_2 \cdot Z$, for example, dichlorohydrin and dibromohydrin, or corresponding epoxide compound (obtainable by splitting off hydrogen halide) of the formula

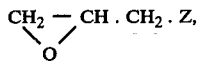

e.g. epichlorohydrin or epibromohydrin. Another example of such a bifunctional compound is 1,2 - 3,4-diepoxybutane of the formula

An example of a trifunctional cross-linking agent (which is an epoxide compound corresponding to a compound of the formula $$X \cdot \overset{Y}{A_2} \cdot Z)$$

is

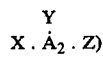

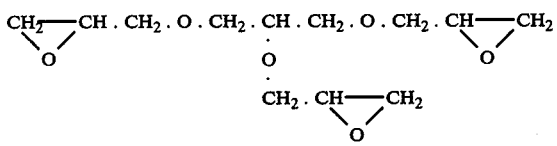

The polysaccharide or the polysaccharide derivative is reacted with such a quantity of an at least bifunctional cross-linking agent that a water-insoluble gel is formed, i.e. a practically infinite three-dimensional network which exhibits the desired properties. One skilled in this art can readily establish empirically a suitable relationship between the quantities of different polysaccharides or polysaccharide derivatives and cross-linking agent.

For the purpose of obtaining cross-linking bridges which are bound to the polysaccharide chains over ester bonds, the polysaccharide or the polysaccharide derivative can be reacted in a manner known per se with, for example, aliphatic or heterocyclic or aromatic dicarboxylic acids or reactive derivatives thereof, e.g. with dicarboxylic acid dichlorides (e.g. of succinic acid or of adipic acid) or for example, with diisocyanates or diisothiocyanates. Other cross-linking agents may also be used.

The cross-linking reaction, in addition to bridge-building, also often results in the introduction of monofunctionally bound (i.e. singly bound) substituents (mono-ethers, mono-esters etc.) from the cross-linking agent, i.e. only one reactive group in the at least bifunctional bridge-building agent has reacted with a hydroxyl group in a polysaccharide chain whilst the other reactive group or groups in the bridge-forming agent have e.g. instead reacted with, e.g. water to form, e.g. hydroxyl groups or carboxyl groups, etc. Consequently, the polymer product most frequently presents also monofunctionally bound substituents originating from the bridge-building agent; e.g. $-O \cdot CH_2 \cdot CH(OH) \cdot CH_2OH$ when the bridge-building agent is epichlorohydrin, and $-O \cdot CH_2 \cdot CH(OH) \cdot CH_2 \cdot O \cdot (CH_2)_4 \cdot O \cdot CH_2 \cdot CH(OH) \cdot CH_2OH$ when the bridge-building agent is 1,4-butandiol-diglycideether or, e.g. $-O \cdot CO \cdot (CH_2)_{n_1} \cdot COOH$ when the bridge-building agent is a dicarboxylic acid dichloride.

The polymeric gel product can be obtained in particle form either by producing the polymer in the form of large pieces (bulk polymerization) and then disintegrating said product, e.g. by grinding, or by producing the product by bead polymerization techniques in the form of spherical particles. In this latter case, the reaction mixture is dispersed to droplet form in an inert liquid which is immisible therewith, whereafter the gel particles formed by the reaction in the droplets are recovered. Particles having a spherical shape are preferably used. The desired particle size can be obtained by fractionating the particles, e.g. by screening the same.

The gel product obtained can be substituted with different groups, e.g. for controlling the rate with which the particles are degraded by α-amylase in blood plasma. For this purpose, hydroxyl groups in the polysaccharide chains may be substituted with substituents, e.g. of the aforementioned type such as lower alkyl, lower carboxyalkyl, lower hydroxyalkyl and/or lower alkanoyl. The substituents may, for example, be ether bound and/or ester bound to the polysaccharide chains.

For the purpose of controlling the rate of degradation of the gel particles in blood plasma, the particles can be subjected to partial hydrolysis in vitro (e.g. with an acid or with α-amylase) prior to or during the preparation of the suspension. This partial hydrolysis of glucosidic linkages is continued until the gel particles have obtained the desired properties.

In accordance with the invention, at least one radioactive substance is included in the diagnostic agent. This agent has the form of an intravascular administratable substance. For example, it may be a radioactive isotope of an inert gas such as xenon or krypton, or a substance which contains a radioactive isotope of iodine or phosphorus, such as sodium iodide or sodium phosphate, or a substance which contains radioactive technetium, e.g. sodium pertechnetate, or e.g. a substance which contains a radioactive isotope of chromium, indium, gold, yttrium, ytterbium, cerium, cobalt, carbon or hydrogen. A large number of such substances containing radioactive isotopes suitable for the intended purpose are known to those skilled in this art. Two or more different radioactive isotopes may also be used. The radioactive substance or substances are present in the diagnostic agent in a concentration and a degree of radioactivity which is sufficient to enable the relevant diagnosis to be made.

In accordance with the invention, the radioactive substance or substances may be in mixture with the minute particles. The substance may, e.g., exist in the form of extremely minute, insoluble particles (e.g. of the same size or smaller than the polysaccharide-based particles) optionally on an inorganic or organic carrier material. The radioactive substance may also be a water-soluble substance. It may be dissolved in the physiologically acceptable aqueous liquid in the suspension. In this respect, conventional radioactive substances for intravascular use are normaly used.

In general, however, the radioactive substance is bound to and/or enclosed in the minute particles. For the purpose of enclosing the radioactive substance in the particle, a radioactive substance, which is insoluble in the aqueous suspension liquid or has a very low solubility therein, may be precipitated out in the swollen gel particle or suspended in the reaction mixture when the polysaccharide is cross-linked to a three-dimensional network. In this case, the radioactive substance may also be bond to an insoluble inorganic or organic carrier, which may be adsorbed on the particles.

Conventional methods may be used for binding the radioactive substance to the particles, for example whilst utilizing the hydroxyl groups of the particles.

The radioactivity of the particles may originate from radioactive technetium, which can be readily incorporated in the particles with a high degree of labelling and with very slight or no leaking of soulble radioactive material, by adding to an aqueous suspension of the particles radioactive sodium pertechnetate and a reduction agent such as stannous chloride, soduim thiosulphate or sodium dithionite in one or more steps.

The diagnostic agent is administered in quantities sufficient to enable, in each individual case, the desired effect to be obtained. In general, the quantity of agent administered (calculated for each individual) corresponds to 0.1 to 2,000 mg of particles, e.g. 0.5 to 200 mg of particles and is dependent upon the examination to be carried out, e.g. the region of blood vessels to be examined and possibly to be clogged. For example, the quantity may be in the range of from 0.001 mg to 50 mg, preferably 0.01 mg to 25 mg, for example 0.05 mg to 10 mg of particles per kilogram of body weight.

The concentration of the particles in the suspension may be varied within wide limits, depending upon the intended use. For example, it may be more than 0.01 mg, e.g. more than 0.1 mg, such as more than 1 mg of particles per 1 ml of suspension, and e.g. less than 200 mg, e.g. less than 50 mg, such as less than 25 mg of particles per 1 ml of suspension. The physiologically acceptable aqueous liquid in which the particles are suspended may be liquids normally used for intravascular injection, (e.g. physiological sodium chloride solution, i.e. 0.9 per cent aqueous solution of NaCl) or aqueous solutions of the salts occurring in the blood plasma. In some cases glucose or sorbitol solutions, e.g. 5 per cent aqueous solutions thereof, may be used. Other physiologically acceptable substances may be added to the suspension, e.g. surcrose or dextran.

Preferably, sterile suspensions of the particles are used. Sterilization can be effected by heat treatment e.g. autoclaving, or by adding substances which prevent the growth of microorganisms. The suspensions may also be prepared aseptically.

The diagnostic agent is intended to be administered intravascularly, i.e. preferably in blood vessels, although it may also be administered, for example, in the lymph vessels.

In accordance with one embodiment of the invention, the particles of the agent may clog the finer vessels subsequent to intravascular administration of said agent, thereby to cause the flow of blood in the vessel to be impeded, so that the retention time of the radioactive substance in the vessel system in question is prolonged or the passage travelled by said substance redirected. When the diagnostic agent is administered, the particles of the agent and the radioactive substance are preferably held in the same portion of the blood vessel and preferably upstream of the finest vessels, as seen in the flow direction.

In accordance with another embodiment of the invention, the radioactivity labelled particles of the agent are smaller than the diameter of the finest vessels, thereby enabling the diagnostic agent to be used, for example, to measure the rate of flow of the blood and the blood volume. These measurements may be performed in a manner known per se.

By means of the present invention it is possible to satisfactorily fill a vessel system or a portion of a vessel with a radioactive substance with a prolonged retention time of the radioactive substance in said vessel portion or the system in question, in a manner which is free from risk, owing to the favourable properties of the particles, inter alia the soft gel consistency of the particles, and owing to the fact that the three-dimensional network of said particles is water-swollen and that the rate at which the particles are degraded enzymatically into water-soluble fragments, can be varied in a reproducable and determinable manner, which can be controlled precisely both in vitro and in vivo. (This is in contrast to previously known particles, including albumin microspheres, which are digested irregularly mainly be phagocytosis in vivo. Currently used albumin particles are not significantly digested in cell-free body fluids.)

Thus, with the diagnostic agent according to the invention it is possible, in comparison with previously known methods, to obtain improved and new diagnostic results in a manner free from risk.

The invention also relates to an auxiliary agent for use when preparing the relevant diagnostic agent for intravascular administration comprising minute particles, preferably having a particle size in the order of magnitude of 0.1 - 300 $\mu$ m, consisting of a polysaccharide built up of glucose units, or a physiologically acceptable derivative of said polysaccharide. The auxiliary agent according to the invention is characterized in that the particles consist of a water-insoluble but hydrophilic, swellable, three-dimensional network of molecules of the polysaccharide or derivative thereof cross-linked with bridges having bonds of a covalent nature, said network being degradable by $\alpha$-amylase in blood plasma into water-soluble fragments directly or subsequently to a preceding splitting-off of possibly occurring substituents, preferably glucoside-bound and/or ester-bound substituents, in the polysaccharide by the action of an enzyme, preferably glucosidase and/or esterase, in blood plasma.

disclosures disclousres made in the aforegoing with respect to the minute particles in conjunction with the diagnostic agent also apply with respect to the particles of the auxiliary agent.

The invention also relates to a method of effecting a diagnosis with the aid of radioactive substances, in which a diagnostic agent is intravascularly administered which consists of or contains a suspension of minute particles, preferably particles having a size in the order of magnitude of 0.1 to 300 μm, consisting of a polysaccharide built up of glucose units or a physiologically acceptable derivative of said polysaccharide in a physiologically acceptable aqueous liquid, said suspension also comprising a radioactive substance which is bound to and/or enclosed in and/or exists in mixture with the minute particles, whereafter the radioactive radiation is measured over the relevant body portion or on a sample taken from said body (e.g. an intravascularly taken sample).

The method according to the invention is characterized in that the particles comprise a water-insoluble but hydrophilic, swellable, three-dimensional network of molecules of the polysaccharide or of the derivative thereof cross-linked by bridges which have bonds of a covalent nature, said network being degradable by α-amylase in blood plasma to water-soluble fragments directly or subsequent to a preceding splitting-off of possibly occurring substituents, preferably glucoside-bound and/or ester-bound substituents, in the polysaccharide, under the action of an enzyme, preferably glucosidase and/or esterase, in blood plasma.

The disclosures made in the aforegoing with respect to the minute particles etc. in conjunction with the diagnostic agent and the auxiliary agent also apply with respect to the particles etc. in conjunction with the method of effecting a diagnosis. Particularly favourable results are obtained with the method according to the invention owing to the favourable properties of the particles.

The invention will now be illustrated by means of a number of examples.

EXAMPLE 1

333 g of soluble starch having a molecular weight ($M_w$) of approximately 20,000 were dissolved in 533 ml of water containing 53 g of sodium hydroxide and 2 g of sodium borohydride. Subsequent to being stirred for four hours, the solution was allowed to stand for two days with a layer of octanol on the surface thereof (about 0.5 ml). A clear solution was obtained.

In a cylindrical reaction vessel provided with a thermometer, a cooler and agitator there were dissolved 20 g of Gafac(R) PE 510 (a complex organic phosphoric acid ester which served as an emulsion stabilizer and which is obtainable from General Aniline Film Corp.) in one liter of ethylene dichloride at room temperature, whereafter the previously prepared starch solution was added. The mixture was stirred at a speed such that the water phase was dispersed to droplet form of the desired magnitude in the ethylene dichloride phase. The size of the droplets formed upon agitation of the starch suspension in ethylene dichloride was controlled with the aid of a microscope. After adjusting the speed of the agitator to 1100 rpm, which gave an average droplet size of 70 μm, 40 g of epichlorohydrin were added.

After a reaction time of 16 hours at 50° C, the product was poured into 5 liters of acetone and allowed to settle. The supernatent liquid was drawn off and the product was slurried in 5 liters of acetone. The acetone was drawn off, 8 liters of water were added and the pH adjusted to 5, by adding acetic acid. The product was then slurried a further 4 times in 8 liters of water and five times in 5 liters of acetone, whereafter the product was dried in vacuum at 50° C for two days, The product weighed 241 g.

The polymer particles were insoluble in water but swelled in water to gel form, the gel particles containing 83 per cent by weight of water. The degree of substitution was about 35%.

Part of the product was suspended well in water. The suspension was then screened by water-streaming on screens having a mesh size of 100 μm, 80 μm, 56 μm, 40 μm and 25 μm. The particles remained on the different screens in accordance with the following weight distribution (the weight are given in dry weight):

| Mesh size in μm | weight (g) |
| --- | --- |
| 80 | 7.9 |
| 56 | 45 |
| 40 | 4.9 |
| 25 | 11.2 |

The fractions were washed with distilled water, and were then washed free of water with acetone and dried in a vacuum at 50° C for two days.

EXAMPLE 2

With respect to products prepared in the manner disclosed in Example 1 but with varying quantities of epichlorohydrin, the effect of the quantities of epichlorohydrin used, on the degradation of the particles by means of α-amylase was examined in the following manner:

7 mg of particles having a size which, when wet-screening the particles in accordance with Example 1, passed through a screen having a mesh size of 40 μm but which remained on a screen having a mesh size of 25 μm, were weighed in a polypropylene vessel and slurried in 20 ml of 0.05 M sodium phosphate buffer, pH 7, with 0.05% Tween(R) 20 (wetting agent) (polyoxyethylene-sorbitan-monolaurate from Atlas Chemie GmbH). The beaker was placed under agitation in a bath, the temperature of which was adjusted to 37° C. When the temperature had stabilized, there were added 200 μl of α-amylase from swine pancreas from a stock solution having a concentration of 150,000 IE/1 or 24,000 IE/1 (IE = international units). 500 μ; of sample were pipetted at uniform intervals down in Ellerman tubes containing 2 ml of an 1 per cent aqueous sodium hydroxide solution, whereafter the tubes were centrifuged for 5 minutes. One ml of the supernatant was then pipetted over to a plastic tube, for determining the quantity of substance which, as a result of the effect of the α-amylase, had been released from the particles and had passed into solution.

As a measurement of the rate of degradation, the time was recorded in which half of the mass of the particles was refound in the supernatant. The following result was obtained:

| Epichlorohydrin (quantity in g) | Water content of swelled particle (% weight) | Degree of substitution (in %) | Time (min) with 240 IE α-amylase/1 | Time (min) with 1500 IE α-amylase/1 |
| --- | --- | --- | --- | --- |
| 20 | ~96 | | <5 | <3 |
| 25 | 93 | ~20 | 19 | 8 |
| 30 | 85 | 29 | 26 | 8.5 |
| 40 | 83 | 36 | 38 | 15.5 |
| 45 | 80 | 40 | 50 | 21 |
| 50 | 76 | 42 | 73 | 30 |

-continued

| Epichloro-hydrin (quantity in g) | Water content of swelled particle (% weight) | Degree of sub-stitution (in %) | Time (min) with 240 IE α-amylase/1 | Time (min) with 1500 IE α-amylase/1 |
| --- | --- | --- | --- | --- |
| 60 | 74 | | | 62 |

When the amount of epichlorohydrin was 60 g, only 25% of the mass of the particles passed into solution in two hours with 240 IE α-amylase/1.

EXAMPLE 3

1.0 g of dry particles produced in accordance with Example 1 but at an agitator speed of 1500 rpm and having a size which, when wet-screened, passed through a screen having a mesh size of 40 μm but remained on a screen having a mesh size of 25 μm, were swollen in 30 ml of water. 0.4 g of acetic acid anhydride dissolved in 5 ml of tetrahydrofuran was added dropwise to the particle suspension over a period of 10 minutes (the pH being kept at 8.5 – 9 by addition of 1 M aqueous NaOH solution), whereafter the suspension was neutralized. The gel grains were then washed with distilled water and acetone, and then dried. The water-swollen particles contained approximately 85% by weight of water. The total degree of substitution was about 50%.

Hydrolysis with 0.1 N sodium hydroxide and titration with 0.1 N hydrochloric acid gave 1.51 mmol of acetyl per gram of dry product. When degrading with α-amylase in accordance with the method described in Example 2, half of the mass of the particles were found in the supernatant after 6 hours with 240 IE α-amylase per liter and after 1 hour and 9 minutes with 1500 IE α-amylase per liter, respectively. For the unsubstituted starting product, half of the mass of the particles was found in the supernatant after 40 minutes with 240 IE α-amylase per liter and after 15 min with 1500 IE α-amylase per liter, respectively. Thus the substitution with acetyl groups had considerably increased the degradation time in the presence of α-amylase in vitro.

EXAMPLE 4

84 g of carboxymethyl starch having a substitution degree of 20% and a molecular weight ($\overline{M}_w$) of about 20,000 were dissolved in 38 ml of water containing 13.7 g of sodium hydroxide and 0.05 g of sodium borohydride. Subsequent to being agitated for four hours, the solution was allowed to stand for 2 days with a layer of octanol on the surface thereof (some few drops). A clear solution was obtained.

In a cylindrical reaction vessel provided with a thermometer, a cooler, and an agitator, there were dissolved 20 g of Gafac$^{(R)}$ PE 510 (a complex organic phosphoric acid ester which serves as an emulsion stabilizer) in 265 ml of ethylene dichloride at room temperature, whereafter the previously prepared starch solution was added. The mixture was agitated at a speed such that the water phase dispersed to droplets of the desired size in the ethylene dichloride phase. The size of the droplets formed in the starch suspension in ethylene dichloride upon said agitation was controlled with the aid of a microscope. Subsequent to adjusting the agitating speed to 1500 rpm, 10.3 g of epichlorohydrin were added.

After 18 hours reaction time at 50° C the product was poured in 2 liters of acetone and allowed to settle. The supernatant was drawn off and the product slurried in 2 liters of acetone. The acetone was drawn off, 2 liters of water were added and the pH adjusted to 5 with acetic acid. The product was slurried 4 times with distilled water admixed with 0.5 g of sodium azide, and 5 times with 1250 ml of acetone, whereafter the product was dried in vacuum at 60° C for 2 days. The product weighed 69 g. The particles were insoluble in water but swelled in water to gel particles, the particles containing about 90% by weight of water. When degraded with α-amylase in accordance with the method described in Example 2, half of the mass of the particles was found in the supernatant after 4.5 and 2.5 hours respectively with α-amylase content 240 and 1500 IE/1 respectively.

EXAMPLE 5

2 g of dry particles were prepared in the manner described in Example 1, but with an agitating speed of 330 rpm and swollen particle size which passed through a screen having a mesh size of 125 μm but which remained on a screen having a mesh size of 100 μm. The particles were stirred in 25 ml of 0.1 M hydrochloric acid at 20° C. A sample amounting to about 0.3 g of particles was taken at different intervals of time, said samples being centrifuged and washed with distilled water 3 times and treated with acetone and dried in a vacuum at 50° C for 16 hours. The time taken for half the mass to degrade to water-soluble fragments under the action of α-amylase as described in Example 2 was then determined. The following results were obtained:

| Time for hydrochloric acid treatment (hours) | Degradation time (min) with 1500 IE α-amylase/1 |
| --- | --- |
| 0 | 60 |
| 3 | 52 |
| 6 | 33 |
| 19 | 8 |

EXAMPLE 6

16 g of a dry product prepared in accordance with Example 1 having a particle size which, when wet-screened, passed through a screen having a mesh size of 40 μm but which remained on a screen having a mesh size of 25 μm, were swollen and suspended in 400 ml of distilled water. 0.85 g of propylene oxide was added and the pH adjusted to 12 with 2 M sodium hydroxide. The suspension was maintained at 50° C and agitated for 24 hours, whereafter the suspension was neutralized with acetic acid, washed with water and wet-screened with water. The fraction which passed through the screen having a mesh size of 40 μm but which remained on a screen having a mesh size of 25 μm was recovered. 2.5 g product was obtained. The product was insoluble in water but swelled in water to gel particles, said particles containing approximately 80% by weight of water. The total degree of substitution was 40%.

EXAMPLE 7

An experiment was carried out in the manner disclosed in Example 1, but instead of epichlorohydrin, there were added 90 g of 1,4-butandioldiglycidyl ether and the speed of the agitator was maintained at 1400 rpm, which resulted in an average droplet size of 25 μm. In other respects the experimental conditions were the same as those disclosed with reference to Example 1 and washing and drying were also effected in the manner disclosed in Example 1. 294 g of product were obtained.

The product was insoluble in water, but swelled in water to gel particles, the particles containing about 75% by weight water. (The degree of substitution was estimated to be about 40%.)

10 g of the product were suspended in about 200 ml of water and were subjected to an ultrasonic treatment process. The suspension was then screened by water-screening through screens having mesh sizes of 56 μm, 40 μm and 25 μm. The particles remained on the different screens in accordance with the following weight distribution (the weights are given as dry weight):

| Mesh size (μm) | weight (g) |
|---|---|
| 40 | 2.8 |
| 25 | 4.2 |

The fractions were washed with distilled water and acetone, whereafter they were dried.

EXAMPLE 8

33 g of hydroxyethyl starch having a molecular weight ($\overline{M}_w$) of about 143,000, were dissolved in 54 ml of water containing 5.3 g of sodium hydroxide and 0.2 g of sodium borohydride. Subsequent to a clear solution being formed there were added 2 g of Gafao$_{(R)}$ PE 510 dissolved in 100 ml of ethylene dichloride and the mixture was agitated at a speed such that a suspension of droplets having an average diameter of 50 μm was formed. 4 g of epichlorohydrin were then added and the mixture was stirred for 16 hours at 50° C. The product was poured into acetone and allowed to settle. The acetone was decanted and the product swollen in water. The pH was adjusted to 5 with HCl, whereafter the product was washed with distilled water, acetone and petroleum ether.

The product was then dried at 50° C in vacuum. The product weighed 33.6 g and presented a substitution degree of about 66%. The water-insoluble product swelled in water to gel particle form, the particles containing about 75% by weight of water. 10 g of the product were screened on screens having a mesh size of 80 μm, 56 μm, 40 μm and 25 μm by water screening. The particles remained on the different screens in accordance with the following weight distribution (dry weight):

| Mesh size (μm) | weight (g) |
|---|---|
| 80 | 3.9 |
| 56 | 1.5 |
| 40 | 0.9 |
| 25 | 1.5 |

EXAMPLE 9

4.5 mg of dry, spherical water-insoluble polymer particles (having a size when swollen of 25 - 40 μm) prepared in accordance with Example 1 were swollen and suspended in 3 ml of an isotonic sodium chloride solution. In this way the suspension contained 0.9 million of swollen particles having a diameter of about 25 14 40 μm. 0.5 ml of acidified stannous chloride (5mg of stannous chloride/ml 0.1 N HCl) and 2 ml of sodium pertechnetate (1.36 mCi) were added to the suspension. After 10 minutes reaction time at room temperature, the suspension was centrifuged, whereafter the radioactivity of the particle mass and of the supernatant was measured individually in a radiation detector. It was found that the particle mass contained 1.24 mCi, while the supernatant contained 0.12 mCi, i.e. the labeling degree was 91%. Subsequent to washing the particles in a 0.9% sodium chloride solution, the labelling efficiency was studied chromatographically. This involved applying about 10 μl of the prepared suspension on a thin layer chromatographic plate (Merck silica gel) for the separation in methyl ethyl ketone. No traces of free, unreduced Tc-99m could be discovered. The suspension was also examined in a Burker calculator chamber under a microscope. No conglomeration of the particles could be observed — this in contradistinction to previously known particles which have a pronounced conglomeration tendency.

EXAMPLE 10

100 mg of spherical particles (having a particle size when water swollen of 25 - 40 μm) prepared in accordance with Example 1 were labelled with sodium pertechnetate in the manner described with reference to Example 9, but with varying quantities of stannous chloride and hydrochloric acid. The following labelling degrees were obtained:

| Stannous chloride containing two crystal water (mg) | 1 ml 0.1 M hydrochloric acid | 0.05 ml 0.1 M hydrochloric acid | 0.01 ml 0.01 M hydrochloric acid |
|---|---|---|---|
| 70 | 97 | 96 | 95 |
| 35 | 99 | 97 | 89 |
| 17.5 | 95 | 92 | 92 |
| 8.5 | 90 | 95 | 94 |
| 5.0 | 87 | 90 | 87 |

EXAMPLE 11

100 mg of spherical particles (having a particle size when water swollen of 25 - 40 μm) prepared in accordance with Example 1 were suspended in 5 ml of stilled water. 50 mg sodium dithionite and 10 μl of an aqueous sodium pertechnetate solution containing 0.5 mCi per 10 ml were added to the suspension. After one half hour reaction time at room temperature (20° C), the product was washed and centrifuged and the labelling degree was measured in the manner described in Example 9. A labelling degree of 90% was obtained.

EXAMPLE 12

An anesthetized rabbit was placed in a recumbent position on its back beneath a gamma camera. One ml suspension of particles (500 μCi) prepared in accordance with Example 9 and corresponding to about 300,000 Tc-99m-labelled polymer particles were then injected into the vein of the right ear. Registrations were made at regular intervals. Immediately after the injection, the lungs were visibilized in a pronouncedly satisfactory manner with the possibility of anatomic detailed examination. After approximately 10 minutes the liver, kidneys and bladder could also be visibilized to a certain extent, owing to the fact that the α-amylase enzyme of the body had begun to degrade the polymer. After 30 minutes, the test was terminated by registering the activity of separate organs, there being refound in the lungs 89.6%, in the liver 6.6%, in the kidneys 3.4% and in the muscle tissue 0.4%. During the whole of the registration time, the lower lobe of the right lung could be satisfactorily visibilized, due to low absorption of radioactivity by the liver.

EXAMPLE 13

A dog weighing 30 kg was catheterized via the groin artery, the end of the catheter being placed in the liver artery and the position of said catheter being verified by X-ray examination. 300 mg of particles produced in accordance with Example 1, which particles, when wet-screened passed through a screen having a mesh size of 56 μm but which remained on a screen having a mesh size of 40 μm, were suspended in 20 ml of physiological sodium chloride solution, whereafter 1 ml of a sodium pertechnetate aqueous solution containing an activity of 0.2 millicurie Tc-99m was added. This mixture was introduced into the vessel bed of the liver via the catheter. The radiation over the area of the liver was measured with a radiation detector using so-called rectilinear scanning, and the radiation intensity over different portions of the body portion was photographically registered via an oscilloscope. The photographic image showed the anatomic extension of the vessel bed in greater detail. After approximately 20 minutes further measurements were made. The image obtained showed that the gamma-radiating isotope Tc-99m had now disappeared from the organ in question, and the test could now be repeated with similar results, which is of great value in respect of the physiological studies of experimentally produced changes in the regional blood distribution. The method can also be used for the differential diagnosis of tumours.

EXAMPLE 14

0.3 g dry, spherical, in water insoluble but swellable particles (with a swelled diameter size of 20 - 40 μm) prepared according to Example 1, but with 50 g of epichlorohydrin instead of 40 g mentioned in said example (the water-swollen particles contained approximately 75% (by weight) of water and the total degree of substitution was 40%), were swelled and suspended in 10 ml of a solution of stannous chloride (10 mg $SnCl_2$, $H_2O$) in 10 ml of 0.01 N deaired hydrochloric acid. This mixture was then poured into 10 ml of 1 M sodium acetate-acetic acid buffer of pH 5.0. After a reaction time of 30 min., the mixture was centrifuged and the centrifugate was washed twice with deaired distilled water. After this the particles were suspended in 100 ml of a deaired 10% saccharose solution and 0.1 ml deaired 1 M sodium acetate-acetic acid buffer of pH 5.0 was added. Aliquotes of 1 ml of this suspension were portioned into 5 ml bottles, which were sealed under nitrogen. After addition of 1 ml sodium pertechnetate (1.5 mCi Tc-99m/ml) and shaking for 15 min, sample bottles were centrifuged, and the supernatant was withdrawn, whereafter the radioactivity of the particle mass, the supernatant and the bottle were measured individually in a radiation detector. It was found that the particle mass contained 1.45 mCi, while the supernatant contained 0.03 mCi and the bottle 0.02 mCi, i.e. the labelling degree was 97%.

A dog weighing 20 kg was anaesthetized with pentobarbital (30 mg per kg body weight) by intravenous injection through a brachial vein catheter. A gamma camera was adjusted to detect Tc-99m activity over the lungs. The Tc-99m labelled centent of a bottle (1 ml, 3 mg particles/ml, 1.5 mCi) was injected via the brachial vein catheter. Tc-99m activity in the lungs was immediately observed on an oscilloscope. Sequential photographs of the image of the lungs on the oscilloscope were taken with a Polaroid camera attached to the oscilloscope. A detailed and clear perfusion lung image was obtained immediately following the injection. The image persisted long enough for a through examination of both lungs.

EXAMPLE 15

3 mg dry, spherical, in water insoluble but swellable particles (with a swelled diameter size of 20 - 40 μm) prepared according to Example 1, but with 50 g epichlorohydrin instead of 40 g mentioned in said example (the particles containing approximately 75% (by weight) of water and the total degree of substitution was 40%), were swelled and suspended in 1 ml of 0.1 M acetate buffer of pH 5.0 and autoclaved in a sealed bottle. 0.1 ml of acidified stannous chaloride (1 mg $SnCl_2$, $H_2O$/1 ml 0.01 N hydrochloric acid) was added to 1 ml sodium pertechnetate (2.3 mCi Tc-99m), using aseptic technique (millipore filters). After thorough shaking this solution was added aspectically to the suspension of particles. After 10 minutes reaction time at room temperature the suspension was centrifuged and the labelling degree was measured as described in Example 9 using aseptic tecnique. It was found to be 98%. The particles were then suspended in 1 ml 5% sterile glucose solution using aseptic technique, and injected as a bolus into the right cubital vein of a man aged 65. He was suffering from pulmonary embolism affecting the lower lobe of the right lung. The lung perfusion was visualized by a gamma camera, positioned to cover the chest and upper abdomen. Excellent scans were recorded from several positions, all showing impared perfusion in the area embolized. Repeated scans could be performed during 3 hours, with no detectable radioactivity in the liver, thus permitting close examination of the diseased lung section.

Previously used albumin based particles usually give high liver activity soon after injection, interfering with visualization of the anatomically close right lung while the particles in this example gave no disturbing liver activity when used as a diagnostic agent for the lungs.

What is claimed is:

1. In the known diagnostic agent for intravascular administration into blood vessels composed of radioactively labelled particles suspended in a physiologically acceptable aqueous liquid, said particles having a size so selected that they clog fine blood vessels having a diameter within the range 5–300 μm, the improvement which comprises said particles consisting of a three-dimensional, water-insoluble, hydrophilic, swellable, cross-linked network of polysaccharide substances, said network being composed of a polysaccharide substance selected from the group consisting of starch, amylose, amylopectin, glycogen, and dextrin, cross-linking having been effected by ether bonds that form bridges between polysaccharide substances, said bridges being straight or branched aliphatic saturated hydrocarbon chains substituted with one to six hydroxyl group and containing 3 – 20 carbon atoms and being unbroken or broken with one to six oxygen atoms, the total substitution degree for the polysaccharide being lower than 70% and higher than 5%, said substitution degree being given as the percentage of the number of substituted glucose units with respect to the total number of glucose units present, said three-dimensional network being degradable by the α-amylase in blood plasma into water-soluble fragments and said cross-linked polysaccharide substance swelling to a gel in the presence of water, said gel containing more than 50% and less than 99.5% by weight of water.

2. An agent according to claim 1, wherein the total substitution degree for the polysaccharide is lower than 60% and higher than 10%, said substitution degree being given as the percentage of the number of substituted glucose units with respect to the total number of glucose units present.

3. In the known diagnostic agent for intravascular administration into blood vessels composed of radioactively labelled particles suspended in a physiologically acceptable aqueous liquid, said particles having a size so selected that they clog fine blood vessels having a diameter within the range 5 - 300 μm the improvement which comprises said particles consisting of a three-dimensional, water-insoluble hydrophilic, swellable, cross-linked network of polysaccharide substances, said network being composed of a polysaccharide substance selected from the group consisting of starch, amylose, amylopectin, glycogen, dextrin, or a physiologically acceptable derivative of one of the aforesaid polysaccharides cross-linking having been effected by ether bonds that form bridges between polysaccharide substances, said bridges being straight or branched aliphatic saturated hydrocarbon chains substituted with one to six hydroxyl groups and containing 3 - 20 carbon atoms and being unbroken or broken with one to six oxygen atoms, the total substitution degree for the polysaccharide being lower than 70% and higher than 5%, said substitution degree being given as the percentage of the number of substituted glucose units with respect to the total number of glucose units present, said three-dimensional network being degradable by the α-amylase in blood plasma into water-soluble fragments and said cross-linked polysaccharide substance swelling to a gel in the presence of water, said gel containing more than 50% and less than 99.5% by weight of water.

4. An agent according to claim 3, wherein said polysaccharide derivatives contain as substitutents at least one member selected from the group consisting of 2-hydroxyethyl, 2-hydroxypropyl, 2,3-dihydroxypropyl, acetyl, propionyl, 2-hydroxypropanoyl, succinoyl and glutaroyl.

5. An agent according to claim 3 wherein the total substitution degree for the polysaccharide is lower than 60% and higher than 10%, said substitution degree being given as the percentage of the number of substituted glucose units with respect to the total number of glucose units present.

6. An agent according to claim 3, wherein said cross-linked polysaccharide substance swells to a gel in the presence of water, said gel containing more than 65% and less than 98% by weight of water.

7. An agent according to claim 3, wherein the meshes of said three-dimensional network have a size such that protein molecules of the same size as α-amylase are able to penetrate into the particles in their water-swollen state.

8. An agent according to claim 3 wherein the outer layer of said three-dimensional network is degraded more slowly by α-amylase than the central portion of said network.

9. An agent according to claim 3 wherein said particles are substantially spherical in shape.

10. An agent according to claim 3, wherein said particles have a size of 5 - 60 μm in their water-swollen state.

11. An agent according to claim 3 wherein said three-dimensional network can be degraded by α-amylase into water-soluble fragments having a molecular weight beneath 50,000.

12. An agent according to claim 3 wherein said particles are labelled with a radioactive isotope of technetium.

13. In the known method of effecting a diagnosis with the aid of radioactive substance, in which method there is intravascularly administered into blood vessels a diagnostic agent composed of radioactively labelled particles suspended in a physiologically acceptable aqueous liquid, said particles having a size so selected that they clog fine blood vessels having a diameter within the range 5 - 300 μm and then measuring the radioactive radiation over the relevant portion of the body, the improvement which comprises using particles consisting of a three-dimensional, water-insoluble, hydrophilic, swellable, cross-linked network of polysaccharide substances, said network being composed of a polysaccharide substance selected from the group consisting of starch, amylose, amylopectin, glycogen and dextrin, cross-linking having been effected by ether bonds that form bridges between polysaccharide substances, said bridges being straight or branched aliphatic saturated hydrocarbon chains substituted with one to six hydroxyl groups and containing 3 - 20 carbon atoms and being unbroken or broken with one to six oxygen atoms, the total substitution degree for the polysaccharide being lower than 70% and higher than 5%, said substitution degree being given as the percentage of the number of substituted glucose units with respect to the total number of glucose units present, said three-dimensional network being degradable by the α-amylase in blood plasma into water-soluble fragments and said cross-linked polysaccharide substance swelling to a gel in the presence of water, said gel containing more than 50% and less than 99.5% by weight of water.

14. In the known method of effecting a diagnosis with the aid of radioactive substance, in which method there is intravascularly administered into blood vessels a diagnostic agent composed of radioactively labelled particles suspended in a physiologically acceptable aqueous liquid, said particles having a size so selected that they clog fine blood vessels having a diameter within the range 5 - 300 μm and then measuring the radioactive radiation over the relevant portion of the body, the improvement which comprises using particles consisting of a three-dimensional, water-insoluble, hydrophilic, swellable, cross-linked network of polysaccharide substances, said network being composed of a polysaccharide substance selected from the group consisting of starch, amylose, amylopectin, glycogen, dextrin, or a physiologically acceptable derivative of one of the aforesaid polysaccharides, cross-linking having been effected by ether bonds that form bridges between polysaccharide substances, said bridges being straight or branched aliphatic saturated hydrocarbon chains substituted with one to six hydroxyl groups and containing 3 -

20 carbon atoms and being unbroken or broken with 1 to 6 oxygen atoms,
the total substitution degree for the polysaccharide being lower than 70% and higher than 5%, said substitution degree being given as the percentage of the number of substituted glucose units with respect to the total number of glucose units present,
said three-dimensional network being degradable by the α-amylase in blood plasma, into water-soluble fragments and said cross-linked polysaccharide substance swelling to a gel in the presence of water, said gel containing more than 50% and less than 99.5% by weight of water.

* * * * *